United States Patent [19]

Yoshida et al.

[11] 4,297,096
[45] Oct. 27, 1981

[54] ALKYL, ALKENYL, AND ARYL SUBSTITUTED TRIAZENE COMPOUNDS, THEIR SALTS AND PRODUCTION THEREOF

[75] Inventors: Keizo Yoshida, Ibaraki; Hirokazu Tanaka, Takarazuka; Masanori Okamoto; Eiko Iguchi, both of Osaka; Masanobu Kohsaka, Sakai; Hatsuo Aoki, Ikeda; Hiroshi Imanaka, Osaka, all of Japan

[73] Assignee: Fujisawa Pharmaceutical Co. Ltd., Osaka, Japan

[21] Appl. No.: 143,310

[22] Filed: Apr. 24, 1980

Related U.S. Application Data

[63] Continuation-in-part of Ser. No. 18,158, Mar. 7, 1979, abandoned, and a continuation-in-part of Ser. No. 92,476, Nov. 8, 1979, abandoned.

[51] Int. Cl.$^3$ .................. A01G 47/08; A01G 51/00; C07C 107/02; C12P 13/00
[52] U.S. Cl. ................................. 435/128; 260/140; 260/143; 424/226; 564/248; 564/268
[58] Field of Search ............... 260/143, 140; 195/113; 435/128; 564/268, 248

[56] References Cited

U.S. PATENT DOCUMENTS

| 3,714,351 | 1/1973 | Gubler | 424/226 |
| 3,907,767 | 9/1975 | Hess et al. | 260/140 |
| 3,989,680 | 11/1976 | Miesel | 260/140 |

FOREIGN PATENT DOCUMENTS 7001059 7/1970 Netherlands .................. 260/140

OTHER PUBLICATIONS

Schroeder et al., Arzneimittelchemie II, pp. 74, 75, 79, 80, (1976).

Primary Examiner—Floyd D. Higel
Attorney, Agent, or Firm—Bierman & Bierman

[57] ABSTRACT

A new triazene compound of the formula:

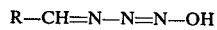

R—CH=N—N=N—OH wherein R is alkyl, alkenyl or aryl and its pharmaceutically acceptable salts thereof. The production and use of such compounds are also disclosed. The compounds are useful as smooth muscle relaxants and hypotensives.

11 Claims, No Drawings

ALKYL, ALKENYL, AND ARYL SUBSTITUTED TRIAZENE COMPOUNDS, THEIR SALTS AND PRODUCTION THEREOF

This is a continuation-in-part of copending applications, Ser. No. 18,158 filed on Mar. 7, 1979, now abandoned and Ser. No. 92,476 filed on Nov. 8, 1979, now abandoned.

This invention relates to new triazene compounds. More particularly, it relates to new triazene compounds which have relaxation activity on smooth muscle and hypotensive activity and their pharmaceutically acceptable salts, to a process for the preparation thereof and to pharmaceutical composition comprising the same.

Accordingly, one object of this invention is to provide new triazene compounds and their pharmaceutically acceptable salts which have relaxation effect on muscle and hypotensive activity, and are useful for the treatment of diseases such as cardiovascular disease, bronchial disease or hypertension in human beings.

Another object of this invention is to provide a process for preparing the triazene compounds by synthesis or fermentation of a FR-900184 and/or FR-900190 substance-producing strain belonging to the genus Streptomyces in a nutrient medium.

A further object of this invention is to provide a pharmaceutical composition comprising the triazene compounds or the pharmaceutically acceptable salt thereof as an active ingredient.

Still further object of this invention is to provide a therapeutical method of treating cardiovascular diseases, bronchial diseases and hypertension by administration of the triazene compounds or the pharmaceutically acceptable salt thereof.

Triazene compound of this invention can be represented by the following formula:

$$R-CH=N-N=N-OH \quad (I)$$

wherein R is alkyl, alkenyl or aryl and its pharmaceutically acceptable salt.

The triazene compound represented by the formula (I) can also be represented by the following tautomeric formula (II):

$$RCH=N-NH-N=O \quad (II)$$

and it is understood that the formula (I) and (II) lie in the relation of tautomerism, with each other. Then, as to the structural expression, it is to be noted that the formula (I) is used in the description of the invention for convenience' sake.

The definition for R of the formula (I) is more particularly explained as follows. Alkyl may be lower ($C_1-C_6$) ones (e.g. methyl, ethyl, propyl, isopropyl, butyl, pentyl, hexyl, etc.). Alkenyl means unsaturated hydrocarbon residue and preferably includes higher ($C_6-C_{18}$) alkatrienyl (e.g. 1,3,5-decatrienyl, 1,3,6-decatrienyl, etc.). Aryl includes phenyl, tolyl, naphtyl and the like.

The pharmaceutically acceptable salts of the triazene compound (I) may include a salt with a base such as an inorganic base (e.g. sodium hydroxide, potassium hydroxide, calcium hydroxide, ammonia, etc.), and an organic base (e.g. ethanolamine, triethylamine, dicyclohexylamine, etc.).

The triazene compound (I) can be prepared by the synthetic process and/or fermentation process, the details of which are illustrated as follows.

SYNTHETIC PROCESS

The synthetic process can be illustrated by the following reaction scheme:

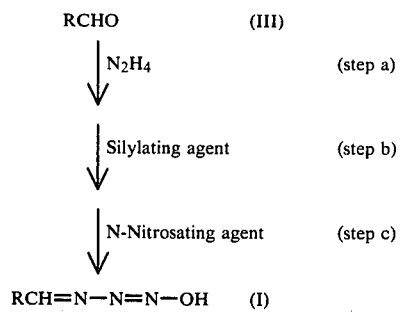

wherein R is as defined above.

In this process, the object compound (I) can be prepared by reacting the compound (III) with hydrazine, silylating agent and then N-nitrosating agent.

The starting compound (III) includes known and new ones. The new compound, for example, 2,4,7-undecatrienal, 2,4,6-undecatrienal can be prepared according to processes conventionally used for synthesis of saturated or unsaturated aldehydes, and the particulars of preparation process thereof will be illustrated in the working Examples of this specification.

Particulars of reactions of this process are illustrated in the following.

STEP (A)

This step is conducted by reacting the compound (III) with hydrazine.

The reaction is usually conducted under mild condition, for example, under cooling to at around ambient temperature in a conventional solvent such as alcohol (e.g. methanol, ethanol, propanol, etc.), tetrahydrofuran, organic acid (e.g. acetic acid, etc.), monoglyme and the like.

STEP (B)

This step is conducted by reacting the resultant product produced in the above step (a), i.e. hydrazone derivative with a silylating agent.

The reaction is conducted under mild condition, for example, under cooling to at around ambient temperature in a solvent such as ether, tetrahydrofuran, dichloromethane, chloroform, benzene, toluene and the like.

The silylating agent which can be used in this step may include a convientional organosilane compound such as trialkylhalosilane (e.g. trimethylchlorosilane, etc.), trialkylsilylamide (e.g. N,N-bis-trimethylsilylacetamide, etc.), dialkyldihalosilane (e.g. dimethyldichlorosilane, etc.), alkyltrihalosilane (e.g. methyltrichlorosilane, etc.), dialkylarylhalosilane, triarylhalosilane, dialkylaralkylhalosilane, dialkoxydihalosilane, trialkoxyhalosilane and the like.

This reaction can preferably be carried out in the presence of conventional organic base such as triethylamine, trimethylamine, pyridine and the like.

STEP (C)

This step is conducted by further reacting the silylated compound produced in the above step (b) with a nitrosating agent.

The reaction is conducted under mild condition, for example, under cooling in a conventional solvent such as dichloromethane, chloroform, carbon tetrachloride, tetrahydrofuran, ether and the like.

The nitrosating agent which can be used in this step may include nitrogen trioxide and the like.

The reaction can preferably be carried out in the presence of an organic base such as trimethylamine, triethylamine, pyridine and the like.

The object compound (I) thus produced can be isolated and purified in a conventional manner, for example, salt formation, extraction, chromatography, recrystallization, etc.

FERMENTATION PROCESS

The following two object compounds of this invention, which are referred to as FR-900184 and FR-900190 substances, respectively can also be prepared by fermentation process.

FR-900184 substance:

$$CH_3-CH_2-CH_2-CH_2-CH=CH-CH=CH-CH=CH-CH=N-N=N-OH$$

[1-Hydroxy-3-(trans, trans, trans-2,4,6-undecatrienylidene)triazene]

FR-900190 substance:

$$CH_3-CH_2-CH_2-CH=CH-CH_2-CH=CH-CH=CH-CH=N-N=N-OH$$

[1-Hydroxy-3-(trans, trans, trans-2,4,7-undecatrienylidene)triazene]

More particularly, the FR-900184 and FR-900190 substances can be prepared by a fermentation of a FR-900184 and/or FR-900190 substance producing strain belonging to the genus Streptomyces such as *Streptomyces aureofaciens* and the like in a nutrient medium.

Particulars of microorganism used for producing FR-900184 and/or FR-900190 substances and production thereof will be explained in the followings.

MICROORGANISM

The microorganism which can be used for the production of the FR-900184 and/or FR-900190 is a strain belonging to the genus Streptomyces, among which a strain of *Streptomyces aureofaciens* has been newly isolated from a soil sample collected in Tokyo, Metropolis, Japan as a suitable strain of a FR-900184 and/or FR-900190 substance producing strain belonging to the genus Streptomyces.

A culture of the newly isolated living organism has been deposited with and added to a permanent stock culture collection of the American Type Culture Collection, under the number ATCC No. 31442 on Oct. 12, 1978. Further, the same has been deposited with Fermentation Research Institute, Agency of Industrial Science and Technology, Japan, under the number FERM-P 4671. on Oct. 9, 1978.

It is to be understood that the production of the new FR-900184 and/or FR-900190 substance of this invention is not limited to the use of the particular organism described herein, which is given for illustrative purpose only. This invention also includes the use of any mutants which are capable of producing the FR-900184 and/or FR-900190 substance including natural mutants as well as artificial mutants which can be produced from the described organism by conventional means, such as X-rays, ultra-violet radiation, N-methyl-N'-nitro-N-nitrosoguanidine, 2-aminopurine and nitrogen mustard oils and the like.

*Streptomyces aureofaciens* ATCC 31442 has the following morphological, cultural, and biological and physiological characteristics.

1. Morphological characteristics

Microscopic observations were made on cultures which were grown of sucrose-nitrate agar, glycerinasparagine agar, yeast-malt extract agar, oatmeal agar and inorganic salts-starch agar at 30° C. for 10–14 days.

(1) Type of branching of spore-forming hyphae: Monopodial branching
(2) Form of spore-forming hyphae: Retinaculiaperti or Spirals
(3) Number of spores and size of spore: 10–30 spores; $0.4–0.8 \times 0.9–1.6\mu$
(4) Surface appearance of spore: Smooth
(5) Existence of Zoospora: Not observed
(6) Existence of sporangium: Not observed
(7) Formation of spores: At aerial mycelium
(8) Fragmentation of substrate mycelium: Not observed
(9) Existence of scleotium: Not observed 2. Cultural characteristics The following observations were made on cultures which were grown on various media at 30° C. for 10 days.

| Medium | Aerial mass color | Reverse side of colony | Soluble pigment |
| --- | --- | --- | --- |
| Sucrose-nitrate agar | very thin, powdery | colorless, small colonies | none |
| Glucose-asparagine agar | very thin, powdery | yellowish brown small colonies | none |
| Glycerin-asparagine agar | none | dull yellow orange-light brown, small colonies | none or trace |
| Starch-inorganic salts agar | light gray, powdery | yellowish brown-light brown, small colonies | yellowish orange |
| Tyrosine agar | none | light brown-brown, small colonies, slightly wrinkled | none |
| Nutrient agar | none | pale yellow-reddish yellow, flat | none |
| Yeast-malt extract agar | gray or pale yellow, powdery | yellowish brown-brown, small colonies | faint dull orange |
| Oatmeal agar | gray, thin powdery | colorless, small colonies | none or trace of yellow |
| Glucose-peptone gelatin stab | none | colorless-cream, weak growth | none |
| Milk | white, thin powdery | pale yellow, growth on surface | trace |
| Peptone-yeast iron agar | none | pale yellow-colorless, wrinkled colonies | none |

3. Biological and physiological properties
(1) Temperature requirements (on Bennett agar slants): growth from 13° C. to 37° C. (optimum: 26° C.)

(2) Liquefaction of gelatin (on glucose-peptone gelatin stab): extremely weak
(3) Hydrolysis of starch (on starch-inorganic salts agar): negative
(4) Action on milk: no coagulation, weak peptonization
(5) Production of melanoid pigment (on tyrosine agar, peptone-yeast iron agar and tryptone-yeast broth): negative
(6) Utilization of various carbon compounds (on Pridham-Gottlieb basal agar medium):

| L - Arabinose | ± | Chitin | − |
|---|---|---|---|
| Cellulose | − | Glycerin | + |
| D - Fructose | ± | Inulin | − |
| D - Glucose | ± | Lactose | ± |
| D - Galactose | ± | Maltose | ± |
| Inositol | ± | Sodium acetate | − |
| D - Mannose | ± | Sodium citrate | + |
| D - Mannitol | − | Sodium succinate | − |
| L - Rhamnose | ± | | |
| Raffinose | − | | |
| Sucrose | ± | | |
| Salicin | − | | |
| D - Xylose | ± | | |

(+: good utilization, ±: doubtful utilization, −: no utilization)

As a result of looking up the strain possessing the characteristics mentioned above by referring to the literature; namely, "Bergey's Manual of Determinative Bacteriology" eighth edition (1975), "The Actinomycetes" Vol. II (1961) written by S. A. Waksman and "The International Streptomyces Project Reports" written by E. B. Shirling and D. Gottlieb [Cf. International Journal of Systematic Bacteriology Vol. 18, pages 69 and 279 (1968), Vol. 19, page 391 (1969) and Vol. 22, page 265 (1972)], *Streptomyces olivaceus*, *Streptomyces aureofaciens*, *Streptomyces xantholiticus* and *Streptomyces viridifaciens* have been detected as relatively analogous characteristics to those of the strain ATCC 31442. The strain ATCC 31442, however, is different from these analogous species in the following respects.

*Streptomyces olivaceus:*

*Streptomyces olivaceus* shows non-characteristic color in its substrate mycelium, does not produce any soluble pigment in a medium and comparatively utilizes all of the carbon sources.

*Streptomyces aureofaciens:*

*Streptomyces aureofaciens* does not produce any soluble pigment in a medium.

*Streptomyces xantholiticus:*

Growth of aerial mycelia of *Streptomyces xantholiticus* is not abundant. Form of aerial mycelia of *Streptomyces xantholiticus* is different from that of the ATCC 31442 strain. Substrate mycelia of *Streptomyces xantholiticus* shows greenish color.

*Streptomyces viridiofaciens:*

*Streptomyces viridiofaciens* has non-characteristic color in its substrate mycelia. Physiological characteristics of *Streptomyces viridiofaciens* are different from that of the ATCC 31442 strain.

From the above observation, it can reasonably be judged that the ATCC 31442 strain is belonging to the species *Streptomyces aureofaciens*, because *Streptomyces aureofaciens* has mostly similar microbiological characteristics to that of the ATCC 31442. However, it is to be noted that the ATCC 31442 is a new strain in view that it produces new FR-900184 and/or FR-900190 substance, while any strains of the publicly known *Streptomyces aureofaciens* have not been known to produce said FR-900184 and/or FR-900190 substance.

PRODUCTION OF FR-900184 AND FR-900190 SUBSTANCE

The FR-900184 and/or FR-900190 substance are produced by culturing a FR-900184 and/or FR-900190 substance producing strain belonging to the genus Streptomyces, such as *Streptomyces aureofaciens* ATCC 31442 in a nutrient medium, and in this regard it is to be noted that when *Streptomyces aureofaciens* ATCC 31442 is used, said two compounds are simultaneously produced in a culture medium.

In general, FR-900184 and/or FR-900190 are produced by culturing a FR-900184 and/or FR-900190 substance producing strain in a nutrient medium containing assimilable sources of carbon and of nitrogen, preferably under aerobic conditions (e.g. shaking culture, submerged culture, etc.).

The preferred sources of carbon in the nutrient medium are carbohydrates such as glucose, fructose, glycerin and starch. Other sources which may be included are lactose, arabinose, xylose, dextrin, molasses and the like.

The preferred sources of nitrogen are yeast extract, peptone, gluten meal, cottonseed meal, soybean meal, corn steep liquor, dried yeast, etc., as well as inorganic and organic nitrogen compounds such as ammonium salts (e.g. ammonium nitrate, ammonium sulphate, ammonium phosphate, etc.), urea, amino acid and the like.

The carbon and nitrogen sources, though advantageously employed in combination, need not be used in their pure form because less pure materials which contain traces of growth factors and considerable quantities of mineral nutrients, are also suitable for use. When desired, there may be added to medium such mineral salts as calcium carbonate, sodium or potassium phosphate, sodium or potassium chloride, magnesium salt, copper salt and the like. If necessary, especially when the culture medium is foamed remarkably, a defoaming agent such as liquid paraffin, higher alcohol, plant oil, mineral oil and silicones may be added.

As conditions for the production in massive amounts, submerged aerobic cultural condition is preferred for the production of the FR-900184 and/or FR-900190 substance. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of the FR-900184 and/or FR-900190 substance. Accordingly, it is desirable first to produce a vegetative inoculum of the organism by inoculating a relatively small quantity of culture medium with spores or mycelia of the organism and culturing said inoculated medium, and then to transfer the cultured vegetative inoculum aseptically to large tanks. As the medium, in which the vegetative inoculum is produced, there can be used the substantially same as or somewhat different medium from medium utilized for main production of the FR-900184 and/or FR-900190 substance.

Agitation and aeration of the culture mixture may be accomplished in a variety of ways. Agitation may be provided by a propeller or the similar mechanical agitation equipment, by revolving or shaking the fermenter, by various pumping equipment or by the passage of sterile air through the medium. Aeration may be effected by passing sterile air through the fermentation mixture.

The fermentation is usually conducted at a temperature about between 20° C. and 40° C., preferably around 30° C., for a period of 50 hours to 100 hours, which may be varied according to the fermentation conditions and scale.

Thus produced FR-900184 and/or FR-900190 substance can be recovered from the culture medium by conventional means which are commonly used for the recovery of other fermentation products such as antibiotics.

Especially, when *Streptomyces aureofaciens* ATCC 31442 is used, FR-900184 and FR-900190 substance are simultaneously produced in the culture broth. Accordingly, said two compounds may be each separated in a conventional means or alternatively may be isolated as a mixture thereof.

In general, most of the FR-900184 and FR-900190 substance produced are found in the culture filtrate, and accordingly the FR-900184 and FR-900190 substance can be isolated from the filtrate, which is obtained by filtrating or centrifuging the broth, by a conventional method such as concentration under reduced pressure, lyophilization, extraction with a conventional solvent, pH adjustment, treatment with a conventional resin (e.g. anion or cation exchange resin, non-ionic adsorption resin), treatment with a conventional adsorbent (e.g. activated charcoal, silicic acid, silica gel, cellulose, almina), crystallization, recrystallization and the like.

Further, separation of FR-900184 and FR-900190 substance is carried out by a conventional manner such as chromatography (e.g. high pressure liquid chromatography).

In accordance with this invention, the FR-900184 and FR-900190 substance are produced in the culture medium, and accordingly the FR-900184 and FR-900190 substance produced in the culture broth, can be isolated in the free form and when the solution or the concentrate is treated with an alkali metal material (e.g. sodium or potassium hydroxide) during the processes, i.e. extraction, isolation, or purification processes, may be isolated in the form of their alkali metal salts:

The FR-900184 and FR-900190 substance obtained in its free form may also be converted to their salts with a base such as an inorganic base (e.g. sodium hydroxide, potassium hydroxide, potassium or sodium alkoxide, etc.) or an organic base (e.g. ethanolamine, trimethylamine, dicyclohexylamine, etc.) in a conventional manner.

The salts of the FR-900184 and FR-900190 may easily be converted to the free form by treatment with an acid such as a mineral acid (e.g. hydrochloric acid) in a conventional manner.

The FR-900184 and FR-900190 substance as obtained according to the aforementioned processes possess the following physical and chemical properties;

FR-900190 Substance (A) Physicochemical properties as to crystalline FR-900190 substance obtained in the manner as described in the working Example 1

(1) elemental Analysis (%):

C 63.58: H 8.28: N 20.01

(2) Molecular weight: [Mass Spectrometry]

$M^+ = 207$ (3) Molecular formula:

$C_{11}H_{17}N_3O$ (4) Melting point:

125°–128° C. (dec.)

(5) Specific rotation:

$[\alpha]_D^{25} = 0$ (C = 1.0 in methanol)

(6) Ultraviolet absorption spectrum:

$\nu_{max}^{methanol} = 310$ nm ($E_{1cm}^{1\%} = 1710$)

(7) Infrared absorption spectrum:
$\nu_{max}^{nujol} = 3300 - 2400$ (broad), 1630, 1610, 1595, 1570 (shoulder), 1540 (shoulder), 1460, 1410, 1380, 1370 (shoulder), 1260, 1200 (shoulder), 1170, 1150, 1080, 1030, 1010, 970, 900, 875, 860, 830, 730 cm$^{-1}$.

(8) Nuclear magnetic resonance absorption spectrum:
$\delta$(ppm)(CDCl$_3$): 0.90 (3H, t, J=6 Hz), Ca. 1.17–1.67 (2H, m), Ca. 1.83–2.42 (2H, m), 2.88 (2H, m), 5.47 (2H, m), Ca. 6.0–7.0 (4H, m), 8.36 (1H, d, J=9 Hz), 9.00 (1H, broad; this signal disappears in D$_2$O).

(9) Coloring reaction:
Positive: Each reaction with potassium permanganate, iodine vapor and sulfuric acid.
(10) Color of crystals:
Faint yellow
(11) Solubility:
Soluble: Chloroform, ethyl acetate, methanol and acetone
Sparingly soluble: Benzene, hexane and ether
Insoluble: water
(12) Property of substance:
Acidic substance
(13) Thin layer chromatography:
Carrier: Silica gel sheet

| Developing solvent | Rf value |
| --- | --- |
| Benzene-Ethylacetate (3:1) | 0.45 |
| Hexane-Acetone (2:1) | 0.3 |

(B) Physicochemical properties as to crystalline FR-900190 substance obtained in the manner as described in the working Example 2
(1) Elemental Analysis (%):

C 63.88: H 8.28: N 20.09

(2) Molecular weight:

$M^+ = 207$ [Mass Spectrometry]

(3) Molecular formula:

$C_{11}H_{17}N_3O$ (4) Melting point:

100°–102° C.

(5) Specific rotation:
$[\alpha]_D^{25} = 0$ (C = 1.0 in methanol)

(6) Ultraviolet absorption spectrum:

$\lambda_{max}^{methanol} = 300$ nm ($\epsilon = 44,000$)

(7) Infrared absorption spectrum:

$\nu_{max}^{nujol} = 3170$, 2950, 2920, 2860, 2710, 2700~2100 (broad), 2150, 1612, 1580, 1565, 1540 1490 (shoulder), 1458, 1410, 1378, 1365, 1310, 1277, 1255, 1185, 1165, 1080, 1025, 1005, 975, 966, 910, 890, 872, 820, 760 (shoulder), 715, 623 cm$^{-1}$.

(8) Nuclear magnetic resonance absorption spectrum:

$\delta$(ppm)(CDCl$_3$): 0.90 (3H, t, J=6.5 Hz), Ca. 1.18~1.56 (2H, m), Ca. 1.80~2.12 (2H, m), 2.88 (2H, m), 5.45 (2H, m), Ca. 5.9–7.1 (4H, m), 8.36 (1H, d, J=9 Hz), Ca. 10.8~11.6 (1H, broad; this signal disappears in D$_2$O)

(9) Coloring reaction:

Positive: Each reaction with potassium permanganate, iodine vapor and sulfuric acid.

(10) Color of crystals:

Faint Yellow

(11) Solubility:

Soluble: Chloroform, ethyl acetate, methanol and acetone

Sparingly soluble: Benzene, hexane and ether

Insoluble: water

(12) Property of substnace:

Acidic substance

From the result of analysing the crystals mentioned in the above item (A) by a high pressure liquid chromatography in substantially the same conditions as described in the working Example 2, it has been found that the said crystals contain 20% of FR-900184 besides FR-900190. On the other hand, the crystals mentioned in the above item (B) are pure crystals of FR-900190 free of FR-900184.

FR-900184 Substance (A') Physicochemical properties as to crystalline FR-900184 substance obtained in the manner as described in the working Example 1

(1) Molecular weight:

M$^+$ = 207 [Mass Spectrometry]

(2) Specific rotation:

$[\alpha]_D^{25} = 0$ (C = 1.0 in methanol)

(3) Ultraviolet absorption spectrum:

$\lambda_{max}^{methanol} = 342$ nm (E$_{1cm}^{1\%}$ = 1660)

(4) Coloring reaction:

Positive: Each reaction with potassium permanganate, iodine vapor and sulfuric acid (5) Color of crystals:

Faint yellow (6) Solubility:

Soluble: Chloroform, ethyl acetate, methanol and acetone

Sparingly soluble: Benzene, hexane and ether

Insoluble: water (7) Nuclear magnetic resonance absorption spectrum:

$\delta$(ppm)(DMSO-d$_6$): 0.88 (3H, t, J=7.0 Hz), Ca. 1.1-1.6 (4H, m), Ca. 2.13 (2H, m), 5.9–7.5 (6H, m), 8.41 (1H, d, J=9.5 Hz), 13.93 (1H, broad s)

(B') Physicochemical properties as to crystalline FR-900184 substance obtained in the manner as described in working Example 2

(1) Elemental Analysis (%):

C 63.46: H 8.23: N 20.51

(2) Molecular weight:

M$^+$ = 207 [Mass Spectrometry]

(3) Molecular formula:

C$_{11}$H$_{17}$N$_3$O (4) Melting point:

135°–138° C.

(5) Specific rotation:

$[\alpha]_D^{25} = 0$ (C = 1.0 in methanol)

(6) Ultraviolet absorption spectrum:

$\lambda_{max}^{methanol} = 339$ nm ($\epsilon = 43,000$)

(7) Infrared absorption spectrum:

$\nu_{max}^{nujol} = 3150$, 2950, 2920, 2860, 2760, 2700, 2700~2050 (broad), 1593, 1575 (shoulder), 1538, 1520, 1458, 1405, 1378, 1363, 1335, 1300, 1280 (shoulder), 1236, 1200, 1177, 1162, 1142, 1078, 1022, 1010, 933, 920, 893, 850, 715, 650 (shoulder), 630 cm$^{-1}$.

(8) Nuclear magnetic resonance absorption spectrum:

$\delta$(ppm)(CDCl$_3$—CD$_3$OD): 0.90 (3H, t, J=6.5 Hz), Ca. 1.1~1.6 (4H, m), Ca. 2.0~2.3 (2H, m) Ca. 5.9~7.0 (6H, m) 8.31 (1H, d, J=9.7 Hz)

(9) Coloring reaction

Positive: Each reaction with potassium permanganate, iodine vapor and sulfuric acid

(10) Color of crystals:

Faint yellow

(11) Solubility

Soluble: Chloroform, ethyl acetate, methanol and acetone

Sparingly soluble: Benzene, hexane and ether (Insoluble: Water

(12) Property of substance:

Acidic substance

From the result of measuring purity of the crystals mentioned in the above item (A') by a high pressure liquid chromatography in substantially the same conditions as described in the working Example 2, it has been found that the said crystals contain 10% of FR-900190 besides FR-900184. On the other hand, the crystals mentioned in the above item (B') are pure crystals of FR-900184 free from FR-900190.

According to the above physical and chemical properties and the relationship between ultraviolet absorption and nuclear magnetic absorption spectra of FR-900190 and FR-900184 substances, each structure of FR-900190 and FR-900184 should be given as follows:

For FR-900190:

$$CH_3-CH_2-CH_2-CH_2-CH=CH-CH=CH-CH=CH-CH=N-(N_2OH)$$

For FR-900184:

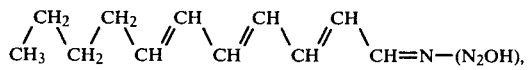

As to the above structure, it is firmly believed that the structure of the terminal triaza group [=N—(N₂OH)] can be assigned to 1-hydroxytriazene [=N—N=N—OH] or alternatively 1-oxotriazane [=N—NH—N=O] structure as a tautomer of the former, and this belief has been confirmed by synthesis of these compounds as exemplified in the working Examples 3 and 4.

The FR-900184 and FR-900190 substance of this invention have relaxation effect on smooth-muscles (e.g. relaxation effect on bronchial muscles, cardiovascular dilating effect) and hypotensive effect.

Accordingly, the object compounds of this invention are useful for bronchodilator which is used for the treatment of bronchial asthma, chronic bronchitis, bronchitis asthmatoid and emphysema, and is also useful for vasodilater which is used for the treatment of coronary insufficiency, angina pectoris and myocardial infarction, and also useful for antihypertensive agent which is used for the treatment of hypertension.

As an example for showing such biological and pharmacological effects of FR-900184 and FR-900190 substance as mentioned above, some pharmacological test data are illustrated in the following.

Test 1: Relaxation effect on rat-aorta

After a 8 weeks-old Sprague-Dawley strain rat was sacrificed, the thoracic aorta was separated. Spiral strips (2 mm×50 mm) were cut from the aorta and suspended in an organ bath containing Tyrode's solution at 37° C., which was aerated with a mixture of 95% oxygen and 5% carbon dioxide.

The maximal relaxation and the duration of the relaxation on the aorta caused by the test compound was determined by a conventional Superfusion method in the following conditions.

Initial tension: 1 g
Velocity of dropping:
(a) Tyrode's solution (10 ml/minute)
(b) Noradrenaline-saline solution (0.6 μg/ml) (0.5 ml/minute)
(c) 300 mM KCl-Tyrode's solution (1 ml/minute)

The results are shown in the following table 1.

TABLE 1

| Test compound (concentration in normal saline) | Relaxation of aorta | | | |
|---|---|---|---|---|
| | against Noradrenaline induced tonus | | against Potassium chloride induced tonus | |
| | Maximal relaxation (mg) | Duration (minutes) | Maximal relaxation (mg) | Duration (minutes) |
| A mixture of FR-900184 and FR-900190 (2:8) (0.1 μg/ 0.2 ml) | 420 | 10 | 200 | 20 |

Test 2: Hypotensive activity in experimental animal

A 8 weeks-old Sprague-Dawley strain rat was anesthetized with uretane (0.7 g/kg, intraperitoneally). Blood pressure was recorded from femoral artery using a transducer coupled to a Biophysiograph 180 system (made by Sanei Sokuki Co., Ltd.). The femoral vein was cannulated to permit intravenus injection of the test compound. The test compound was dissolved in saline and injected in a volume of 0.2 ml. The results are shown in the following table 2.

TABLE 2

| Test compound (Dosage) | Hypotensive effect | |
|---|---|---|
| | Maximal decrease (mm Hg) | Duration (minutes) |
| A mixture of FR-900184 and FR-900190 (2:8) (10 mg/kg) | 60 | 14 |
| A mixture of FR-900184 and FR-900190 (2:8) (1 mg/kg) | 50 | 4 |

(Note) The initial blood pressure: 80 mm Hg

Test 3: Relaxation of dog-coronary artery

The large and small coronary arteries, 2.0 and 0.5 mm in outside diameter respectively, were separated from pentobarbital-anesthetized dog. Spiral strip approximately 15 mm and 5 mm in length were cut from the large and small arteries respectively, and suspended in an organ bath containing Tyrode's solution at 37° C., which was aerated with a gas mixture of 95% oxygen and 5% carbon dioxide. The tonus of the strips was recorded using a force-displacement transducer and a polygraph. After the initial resting tension was adjusted to 1.0 g for the large artery and 100 mg for the small artery, potassium chloride 35 mM was added to the organ bath to increase the tonus of the tension on the large arterial strips to 1.4–1.6 g and that on the small arterial strips to 120–140 mg. The cumulative concentrations of the test compounds were then added, and finally papaverine ($10^{-4}$M) was given to determine the maximum relaxation. The concentration required to produce fifty percent reduction in tonus ((ED50) values) were calculated by interpolation from the mean cumulative dose-response curves (effect by papaverine $10^{-4}$M=100%).

The results are shown in the following table 3.

TABLE 3

| Test compound | kind of artery | ED50 |
|---|---|---|
| A mixture of FR-900184 and FR-900190 (9:1) | large coronary artery | $3.4 \times 10^{-8}$ g/ml |
| A mixture of FR-900184 and FR-900190 (9:1) | small coronary artery | $3.3 \times 10^{-7}$ g/ml |

Test 4: Relaxation effect on guinea pig-trachea

Male guinea pigs weighing 610–800 g were stunned and exsanguinated. Immediately thereafter, the trachea was removed from the animal and cut into small rings being approximately 2 mm in width. Six tracheal chains were connected with fine thread to make a chain. The chains were suspended in a 25 ml organ bath containing Tyrode's solution which was aerated with a gas mixture of 95% oxygen and 5% carbon dioxide. The temperature of bath fluid was maintained at 37° C. The tracheal chain was connected to a force-displacement transducer under initial tension of 0.5–0.6 g, and its tonus was recorded isometrically on a polygraph. Isoproterenol ($1.0 \times 10^{-8}$ g/ml) was added to the organ bath in advance to obtain the maximum relaxation, and the test compound was added to the bath. The concentration required to produce fifty percent reduction in tonus (ED50) was calculated by interpolation from the mean dose-response curve (effect by isoproterenol $1.0\times 10^{-8}$ g/ml = 100%).

TABLE 4

| Test compound | ED50 |
| --- | --- |
| A mixture of FR-900184 and FR-900190 (9:1) | $5.0 \times 10^{-8}$ g/ml |

Test 5: Acute toxicity in mice

1% Aqueous methylcellulose solution containing FR-900190 or FR-900184 substance was given intraperitoneally to male DDY-strain mice, weighing 30 g. $LD_{50}$ value was calculated from the survivals of mice at one week after the administration of the test compound. The results are shown in the following table 5.

TABLE 5

| Test compound | $LD_{50}$ |
| --- | --- |
| A mixture of FR-900184 and FR-900190 (2:8) | >250 mg/kg |
| A mixture of FR-900184 and FR-900190 (9:1) | >250 mg/kg |

The FR-900184 and FR-900190 substance of this invention in admixture with pharmaceutically acceptable carriers can be administered to mammals including human being in a form of a pharmaceutical composition such as capsules, tablets, granules, powders, buccal tablets, sublingual tablets, and solutions.

The pharmaceutically acceptable carriers may include various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent (cellulose, methyl cellulose, hydroxypropylcellulose, polypropylpyrrolidone, gelatin, gum arabic, polyethyleneglycol, sucrose, starch, etc.), disintegrator (e.g. starch, carboxymethyl cellulose, calcium salt of carboxymethyl cellulose, hydroxypropyl-starch, sodium glycolestarch, sodium bicarbonate, calcium phosphate, calcium citrate, etc.), lubricant (e.g. magnesium stearate, aerosil, talc, sodium laurylsulfate, etc.), flavoring agent (e.g. citric acid, mentol, ammonium salt of grycyrlysine, glycine, orange powders, etc.), preservative (sodium benzoate, sodium bisulfite, methylparaben, propylparaben, etc.), stabilizer (citric acid, sodium citrate, acetic acid, etc.), suspending agent (e.g. methyl cellulose, polyvinylpyrrolidone, aluminum stearate, etc.), dispersing agent [e.g. polysolbate 80, emalgen 408 (surface active agent), emasol (surface active agent), etc.], aqueous diluting agent (e.g. water), base wax (e.g. cacao butter, polyethyleneglycol, witepsol, white petrolatum, etc.).

A dosage of the object compounds is to be varied depending on various factors such as kind of diseases, weight and/or age of a patient, and further the kind of administration route. For example, in case of using the object compounds as cardiovasodilator and bronchodilator, preferable dosage for injection can be selected from within a range of about 10 μg − 1 mg/kg/day and dosage unit for oral can be selected from the range of 100 μg − 10 mg, but not limited thereto.

The following Examples are given for the purpose of illustrating this invention.

EXAMPLE 1

A culture medium (100 ml, pH 7.0) containing 1% of potato starch, 1% of gluten meal, 0.5% of corn steep liquor and 0.5% of dried yeast was poured into each of five 500 ml. Erlenmeyer-flasks and sterilized at 120° C. for 20 minutes. A loopful of slant culture of *Streptomyces aureofaciens* ATCC 31442 was inoculated into each of the medium and cultured at 30° C. for 72 hours. The resultant culture was inoculated into a medium (20 liters) containing 3% of soluble starch, 0.5% of gluten meal, 0.5% of peanuts powder, 0.5% of dried yeast and 0.06% of sodium carbonate in 30 liter jar-fermenter which had been sterilized at 120° C. for 20 minutes in advance, and cultured at 30° C. for 72 hours.

After the cultured broth thus obtained was filtered, the filtrate (18 liters) was adjusted to pH 6.8 with 6 N hydrochloric acid and then passed through a column of macroporous nonionic adsorption resin, Diaion HP-20 (Trade name, made by Mitsubishi Chemical Industries Ltd.) (1.5 liters). The column was washed with water (3 liters), and then eluted with methanol (3 liters). After the eluate was dried up under reduced pressure, the resultant residue was chromatographed on a column of silicagel. The column was washed with benzene and then eluted with a mixture of benzene and ethyl acetate (4:1) (500 ml). The eluate was concentrated under reduced pressure to a volume of about 20 ml to give crystalline precipitates, which were collected by filtration (yield: 50 mg).

The crystalline precipitates were subjected to a high pressure liquid chromatography in the following conditions.

Apparatus: An apparatus for liquid chromatography M-6000 A type (made by WATERS ASSOCIATES, INC.)
Stationary phase: Merck RP-18 (10 μm)
Length of column: 500 mm
Internal diameter of column: 8 mm
Mobile phase: 75% of Methanol
Column temperature: Ambient
Column pressure: 2000 psi
Flow rate: 5 ml/minutes
Detector: Ultraviolet Absorption at 254 nm The liquid chromatogram gave the fractions (A) (retention time: 10.10 minutes) and (B) (retention time: 12.40 minutes). The former fraction (A) gave the crystals of FR-900190 (30 mg) and the latter fraction (B) gave the crystals of FR-900184 (3 mg).

EXAMPLE 2

A cultre medium (100 ml, pH 7.3) containing 0.4% of glucose, 0.4% yeast extract and 1.0% of Malt extract was poured into each of two 500 ml. Erlenmeyer-flask and sterilized at 120° C. for 30 minutes. A loopful of slant culture of *Streptomyces aureofaciens* ATCC 31442 was inoculated into the medium and cultured at 30° C. for 72 hours. Each 100 ml of resultant cultured broth was inoculated into a medium (20 liters, pH 7.0) containing 1% of starch, 1% of gluten meal, 0.5% of corn steep liquor and 0.5% of dried yeast in each of two 30 liters.jar-fermenter which had been sterilized at 120° C. for 30 minutes in advance, and cultured at 30° C. for 48 hours. 35 liters of the resultant cultured broth was inoculated into a medium (1760 liters) containing 3% of starch, 0.5% of gluten meal, 0.5% of dried yeast, 0.5% of peanut powder and 0.06% of $Na_2CO_3$ in a 2000 liters.fermentation tank which had been sterilized at 120° C. for 30 minutes in advance, and cultured at 30° C. for 72 hours. The resultant cultured broth was filtered to give a filtrate (1500 liters), which was concentrated under reduced pressure to a volume of 500 liters and extracted with ethyl acetate (620 liters). The extract (370 liters) was concentrated under reduced pressure to a volume of 500 ml. The concentrate was mixed with silica gel (700 g) and subjected to a column chromatography on silica gel. The column was washed with a mixture of hexane and acetone (9:1) (2 liters) and (8:2) (2 liters), and then eluted with a mixture of hexane and acetone (7:3) (3 liters). The eluate was concentrated under reduced pressure to give mixed crystals of FR-900190 and FR-900184 (7:3) (20 g).

250 mg of the mixed crystals were dissolved in acetonitrile (5 ml) and subjected to a high pressure liquid chromatography in the following conditions.

Apparatus: An apparatus for liquid chromatography System 500 (made by WATERS ASSOCIATES, INC.)
Stationary phase: Prep PAK-500 C-18 (made by WATERS ASSOCIATES, INC.)
Length of column: 300 nm
Internal diameter of column: 57 nm
Mobile phase: a mixture of acetonitrile, water and acetic acid (50:50:0.1)
Column pressure: 30 kg/cm$^2$
Column temperature: Ambient
Flow rate: 200 ml/minutes
Detector: Ultraviolet Absorption at 254 nm This chromatography was recycled three times. The liquid chromatogram gave the fractions (A) (retention time: about 28 minutes) and (B) (retention time: about 34 minutes). Each of the fractions was neutralized with sodium bicarbonate, concentrated under reduced pressure and extracted with ethyl acetate, respectively.

The extract obtained from the fraction (A) was washed with water, dried over magnesium sulfate and concentrated to give crystals of FR-900190 (40 mg) which is free of FR-900184.

Further, the extract obtained from the fraction (B) was washed with water, dried over magnesium sulfate and concentrated under reduced pressure to give crystals of FR-900184 (5 mg) which is free of FR-900190.

EXAMPLE 3

(1) To a solution of magnesium metal (8.6 g) in dry tetrahydrofuran (100 ml) was added dropwise ethyl bromide (39 g) in a nitrogen atmosphere at ambient temperature. After the mixture was stirred for an hour at the same temperature, to the mixture was added dropwise a solution of 3-(2-tetrahydropyranyloxy)-1-propyne (50 g) in dry tetrahydrofuran (75 ml) and cuprous cyanide (20 mg). The reaction mixture was stirred for 30 minutes at ambient temperature. To the mixture was added with stirring a solution of 1-bromo-trans-2-hexene (58 g) in dry tetrahydrofuran (75 ml) under ice-cooling. The reaction mixture was stirred for 30 minutes at ambient temperature and concentrated under reduced pressure to give a residue, which was dissolved in diluted hydrochloric acid and extracted with ether. The extract was washed with water, dried over anhydrous magnesium sulfate and concentrated under reduced pressure to give a yellowish oily residue, which was distilled under reduced pressure to give colorless oily 1-(2-tetrahydropyranyloxy)-trans-5-nonen-2-yne (58 g).

b.p.: 142°–144° C./6.5 mmHg
I.R. $\nu_{max}^{film}$: 2310, 2260, 1025 cm$^{-1}$ (2) To a solution of 1-(2-tetrahydropyranyloxy)-trans-5-nonen-2-yne (61.5 g) in methanol (250 ml) was added 4% oxalic acid (250 ml). The reaction mixture was refluxed for 2 hours and concentrated under reduced pressure to give a residue, which was extracted with ether, washed with water, dried over magnesium sulfate and concentrated under reduced pressure to give a yellowish oily residue. The oily residue was distilled under reduced pressure to give colorless oily trans-5-nonen-2-yne-1-ol (37 g).

b.p.: 89°–90° C./3.3 mmHg
I.R. $\nu_{max}^{film}$: 3350, 2310, 2250 cm$^{-1}$ (3) trans-5-nonen-2-yne-1-ol (21 g) was dissolved in liquid ammonia-ether solution (1:1) (200 ml) at −78° C. To the solution was added ammonium sulfate (105 g) and sodium metal (11 g) little by little. The mixture was stirred for 6 hours at −78° C. To the reaction mixture was added ammonium chloride to destroy excess sodium metal. The resultant mixture was stirred at ambient temperature to give a residue, which was dissolved in water. The aqueous solution was extracted with ether, washed with water, dried over anhydrous magnesium sulfate and concentrated under reduced pressure to give a yellowish oily residue, which was distilled under reduced pressure to give colorless oily trans, trans-2,5-nonadien-1-ol (15.3 g).

b.p.: 89°–90° C./10.5 mmHg
I.R. $\nu_{max}^{film}$: 3320, 1665 cm$^{-1}$ (4) To a solution of trans, trans-2,5-nonadien-1-ol (15 g) in chloroform (1500 ml) was added manganese dioxide (150 g). The reaction mixture was stirred for 20 hours at ambient temperature and then filtered. The filtrate was concentrated under reduced pressure to give a yellowish oily residue, which was subjected to a column chromatography on silicagel (developing solvent: chloroform). The fraction containing object compound was concentrated under reduced pressure to give colorless oily trans, trans-2,5-nonadienal (7 g).

b.p.: 70° C./0.3 mmHg
I.R. $\nu_{max}^{film}$: 2730, 1685, 1630 cm$^{-1}$ (5) To a mixture of sodium hydride (2.68 g) and dry benzene (50 ml) was added dropwise triethyl phosphonoacetate (11.5 g) in nitrogen atmosphere. The mixture was stirred for 2 hours at ambient temperature. To the reaction mixture was added dropwise a solution of trans, trans-2,5-nonadienal (7 g) in dry benzene (30 ml). The reaction mixture was stirred for 30 minutes at ambient temperature. The reaction mixture was washed with water. The washings was extracted with ether. The combined organic layer was washed with water, dried over anhydrous magnesium sulfate and concentrated under reduced pressure to give a yellowish oily residue, which was subjected to a column chromatography on silica gel (developing solvent: chloroform). The fractions containing the object compound was concentrated under reduced pressure to give colorless oily ethyl trans, trans, trans-2,4,7-undecatrienoate (4.7 g).

b.p.: 80° C./0.3 mmHg
I.R. $\nu_{max}^{film}$: 1710, 1640, 1617 cm$^{-1}$ (6) To a solution of ethyl trans, trans, trans-2,4,7-undecatrienoate (4.7 g) in dry ether (200 ml) was added with stirring lithium aluminum hydride (1 g) under ice-cooling little by little. The mixture was stirred for an hour at the same temperature. To the resultant mixture was added ether containing water to give insoluble materials, which were removed by filtration. The organic layer was washed with water, dried over magnesium sulfate and concentrated under reduced pressure to give colorless oily trans, trans, trans-2,4,7-undecatrien-1-ol (3.4 g).

b.p.: 105° C./0.3 mmHg
I.R. $\nu_{max}^{film}$: 3340, 1670, 1635 cm$^{-1}$ (7) To a solution of trans, trans, trans-2,4,7-undecatrien-1-ol (3.4 g) in chloroform (300 ml) was added manganese dioxide (30 g). The reaction mixture was stirred for 60 hours at ambient temperature. After the manganese dioxide was removed by filtration, the resultant mixture was concentrated under reduced pressure to give a yellowish oily residue, which was subjected to a column chromatography on silica gel (developing solvent: chloroform) to give colorless oily trans, trans, trans-2,4,7-undecatrienal (2 g).

I.R. $\nu_{max}^{film}$: 2730, 1680, 1637 cm$^{-1}$ (8) To a solution of hydrazine hydrate (10 ml) in methanol (20 ml) was added dropwise with stirring a solution of trans, trans, trans-2,4,7-undecatrienal (2 g) at ambient temperature. The reaction mixture was stirred for 30 minutes and concentrated under reduced pressure to give a residue, which was extracted with ether. The extract was washed with water, dried over magnesium sulfate and concentrated under reduced pressure to give a residue, which was dissolved in dry ether. To the solution was added triethylamine (1.25 g). To the mixture was added with stirring dropwise trimethylchlorosilane (1.33 g) under ice-cooling. The mixture was stirred for 2 hours at ambient temperature. After insoluble materials were removed by filtration, the resultant mixture was concentrated under reduced pressure to give a residue, which was dissolved in dichloromethane. Nitrogen trioxide was passed through the solution for 3 hours under cooling in dry ice-carbon tetrachloride bath. The resultant mixture was poured into ice water. The organic layer was separated, washed with water, dried over anhydrous magnesium sulfate and concentrated under reduced pressure to give a brownish oily residue, which was subjected to a column chromatography on silica gel (developing solvent: chloroform). The fractions containing the object compound was concentrated under reduced pressure to give a residue, which was subjected to a high pressure liquid chromatography to give yellowish crystalline FR-900190 (10 mg.). I.R. spectrum of this crystals was identical with that of FR-900190 obtained in the Example 2.

EXAMPLE 4

(1) To a suspension of sodium hydride (12 g) in dry benzene (300 ml) was added dropwise trans-2-heptenal (22.5 g) with stirring under ice-cooling. The reaction mixture was stirred for 2 hours at ambient temperature. To the mixture was added water and then the organic layer was separated. The aqueous layer was extracted with ether. The combined organic layer was washed with water, dried over magnesium sulfate and concentrated under reduced pressure to give yellowish oily ethyl trans, trans-2,4-nonadienoate (25 g).

b.p.: 100° C./0.25 mmHg

I.R. $\nu_{max}^{CHCl_3}$: 1695, 1635, 1615 cm$^{-1}$ (2) To a solution of ethyl trans, trans-2,4-nonadienoate (25 g) in dry ether (250 ml) was added dropwise lithium aluminum hydride (5 g) with stirring under ice-cooling in the course of an hour. The reaction mixture was stirred for an hour at ambient temperature. To the resultant mixture was added ether containing water and then insoluble materials were removed by filtration. The organic layer was washed with water, dried over magnesium sulfate and concentrated under reduced pressure to give oily trans, trans-2,4-nonadien-1-ol (20 g).

b.p.: 80° C./0.3 mmHg

I.R. $\nu_{max}^{CHCl_3}$: 3610, 3440, 1650 cm$^{-1}$ (3) To a solution of trans, trans-2,4-nonadien-1-ol (20 g) in chloroform (400 ml) was added manganese dioxide (125 g). The mixture was stirred for 11 hours at ambient temperature and then filtered. The filtrate was concentrated under reduced pressure to give an oily residue, which was subjected to a column chromatography on silica gel (developing solvent: chloroform). The eluate was concentrated under reduced pressure to give colorless oily trans, trans-2,4-nonadienal (9 g).

I.R.: $\nu_{max}^{CHCl_3}$: 2740, 1670, 1635, 1600 cm$^{-1}$ (4) To a suspension of sodium hydride (3.3 g) in dry benzene (200 ml) was added dropwise triethyl phosphonoacetate (14.6 g) with stirring under ice-cooling and then the mixture was stirred for 40 minutes at ambient temperature. To the mixture was added dropwise trans, trans-2,4-nonadienal (8.2 g) with stirring and under ice-cooling and then the reaction mixture was stirred for 1.5 hours at ambient temperature. To the resultant mixture was added ice-water. The organic layer was separated and the resultant aqueous layer was extracted with ether. The combined organic layer was washed with water, dried over magnesium sulfate and concentrated under reduced pressure to give yellowish oily ethyl trans, trans, trans-2,4,6-undecatrienoate (12 g).

b.p.: 110° C./0.2 mmHg

I.R. $\nu_{max}^{CHCl_3}$: 1695, 1615, 1587 cm$^{-1}$ (5) To a solution of ethyl trans, trans, trans-2,4,6-undecatrienoate (12 g) in dry ether (300 ml) was added little by little, lithium alminum hydride (1.6 g) with stirring under ice-cooling in the course of 30 minutes and then the mixture was stirred for 30 minutes at ambient temperature. To the resultant mixture was added ether containing water and then insoluble materials was removed by filtration. The filtrate was washed with water, dried over magnesium sulfate and concentrated under reduced pressure to give oily trans, trans, trans-2,4,6-undecatrien-1-ol (7.2 g).

b.p.: 100° C./0.3 mmHg

I.R. $\nu_{max}^{CHCl_3}$: 3610, 3430, 1630 cm$^{-1}$ (6) To a solution of trans, trans, trans-2,4,6-undecatrien-1-ol (7.2 g) in chloroform (300 ml) was added manganese dioxide (50 g) and then the mixture was stirred for 15 hours at ambient temperature. The resultant mixture was filtered and the filtrate was concentrated under reduced pressure to give an oily residue, which was subjected to a column chromatography on silica gel (developing solvent: chloroform). The eluate was concentrated under reduced pressure to give oily trans, trans, trans-2,4,6-undecatrienal (5.5. g).

b.p.: 90° C./0.25 mmHg

I.R. $\nu_{max}^{CHCl_3}$: 2730, 1665, 1610 cm$^{-1}$ (7) The FR-900184 was prepared in substantially the same manner as that of Example 3(8).

EXAMPLE 5

(1) To hydrazine hydrate (50 ml) was added dropwise butyraldehyde (8.17 g) with stirring and under ice-cooling. The reaction mixture was stirred for 2 hours at ambient temperature. To the resultant mixture was added water and then the mixture was extracted with chloroform, washed with water, dried over potassium carbonate and concentrated under reduced pressure to give oily butyraldehyde hydrazone (6.777 g).

(2) To a solution of butyraldehyde hydrazone (6.777 g) in dry ether (30 ml) was added triethylamine (11 ml). To the mixture was added dropwise trimethylchlorosilane (10 ml) under ice-cooling. After the reaction mixture was stirred overnight at ambient temperature, insoluble materials were removed by filtration. The resultant solution was evaporated to dryness to give a residue, which was dissolved in dichloromethane (20 ml). Nitrogen trioxide was passed through the resultant solution for 3 hours at −20° C. The resultant mixture was poured into ice water. The organic layer was separated, washed with water, dried over anhydrous magnesium sulfate and concentrated under reduced pressure to give oily 1-hydroxy-3-butylidenetriazene (1.2 g).

I.R. $\nu_{max}^{film}$: 2140, 1650, 1565 cm$^{-1}$

EXAMPLE 6

To hydrazine hydrate (50 ml) was added dropwise benzaldehyde (10 ml) under ice-cooling. The mixture was stirred for 2 hours at ambient temperature. After water was added to the mixture, the resultant mixture was extracted with chloroform, dried over anhydrous magnesium sulfate and concentrated under reduced pressure to give a residue, which was dissolved in dry ether. To the solution was added triethylamine (13.80 ml) and then trimethylchlorosilane (12.57 ml). The reaction mixture was stirred for 2 hours at ambient temperature. Insoluble materials were removed by filtration. The filtrate was concentrated under reduced pressure to give a residue, to which was added dichloromethane (30 ml). Nitrogen trioxide was passed through the reaction mixture for 3 hours at −20° C. The resultant mixture was poured into ice water. The organic layer was separated, washed with water, dried over magnesium sulfate and concentrated under reduced pressure to give oily 1-hydroxy-3-benzylidenetriazene (1.7 g).

I.R. $\nu_{max}^{film}$: 2145, 1630, 1545 cm$^{-1}$

EXAMPLE 7

To a suspension of FR-900184 (1.05 g) in methanol (20 ml) was added with stirring 28% sodium methoxide methanol solution (1 ml) at ambient temperature. After the reaction mixture was stirred for 10 minutes at the same temperature, insoluble materials were removed by filtration from the mixture. The filtrate was concentrated under reduced pressure to give crystals, which were collected by filtration and dried to give crystals of sodium salt of FR-900184 (500 mg). The same crystals (200 mg) were recovered from the mother liquor.

mp: ~210° C. (dec.)

EXAMPLE 8

To a suspension of FR-900184 (1.05 g) in methanol (20 ml) was added potassium t-butoxide (600 mg) at ambient temperature. After the mixture was stirred for 20 minutes, insoluble materials were removed by filtration from the mixture. The filtrate were concentrated under reduced pressure to give crystals, which were collected by filtration and dried to give crystals of potassium salt of FR-900184 (450 mg). The same crystals (230 mg) were recovered from the mother liquor.

mp: 200°~210° C. (dec.)

We claim:

1. A compound of the formula:

R—CH=N—N=N—OH wherein R is alkyl, alkenyl or aryl or its pharmaceutically acceptable salts.

2. A compound of claim 1, wherein R is alkyl.
3. A compound of claim 2, wherein R is propyl.
4. A compound of claim 1, wherein R is alkenyl.
5. A compound of claim 4, wherein R is alkatrienyl.
6. A compound of claim 5, wherein R is trans, trans, trans-1,3,5-decatrienyl.
7. A compound of claim 5, wherein R is trans, trans, trans-1,3,6-decatrienyl.
8. A compound of claim 1, wherein R is aryl.
9. A compound of claim 8, wherein R is phenyl.
10. A process for the production of FR-900184 substance having the formula:

$$CH_3\text{—}CH_2\text{—}CH_2\text{—}CH=CH\text{—}CH=CH\text{—}CH=CH\text{—}CH=N\text{—}N=N\text{—}OH$$

or FR-900190 substance having the formula $$CH_3\text{—}CH_2\text{—}CH=CH\text{—}CH_2\text{—}CH=CH\text{—}CH=CH\text{—}CH=N\text{—}N=N\text{—}OH$$

or both, which comprises culturing a FR-900184 and/or FR-900190 producing strain belonging to the genus Streptomyces in an aqueous nutrient medium under aerobic condition and recovering FR-900184 or FR-900190 or both substances from the resultant cultured broth.

11. A process for the preparation of the compound of the formula

R—CH=N—N=N—OH wherein R is alkyl, alkenyl or aryl or its pharmaceutically acceptable salts, which comprises reacting a compound of the formula

RCHO wherein R is the same as defined above, with hydrazine, reacting the resultant hydrazone derivative with a silylating agent taken from the class consisting of trialkylhalosilane, trialkylsilylamide, dialkyldihalosilane, alkyltrihalosilane, dialkylarylhalosilane, triarylhalosilane, dialkylaralkylhalosilane, dialkoxydihalosilane, and trialkoxyhalosilane and reacting the resultant silylated compound with an n-nitrosating agent.

* * * * *